United States Patent [19]

Green

[11] Patent Number: 4,658,053

[45] Date of Patent: Apr. 14, 1987

[54] PRODUCTION OF ESTERS

[75] Inventor: Michael J. Green, Hull, England

[73] Assignee: BP Chemicals Limited, London, England

[21] Appl. No.: 704,667

[22] Filed: Feb. 25, 1985

[30] Foreign Application Priority Data

Mar. 8, 1984 [GB] United Kingdom ................. 8406126

[51] Int. Cl.$^4$ ..................... C07C 51/12; C07C 67/03; C07C 67/38
[52] U.S. Cl. ................................. 560/234; 260/410.6; 260/410.9 N; 260/410.9 R; 260/413; 560/1; 560/8; 560/92; 560/129; 560/204; 560/243; 560/245; 560/261; 560/263; 560/265; 560/244; 562/406; 562/497; 562/519; 568/877; 568/909
[58] Field of Search ............... 560/234, 263, 261, 243, 560/265, 204, 92, 244, 245, 1, 8, 129; 562/519, 497, 406; 260/410.9 R, 410.9 N, 410.6, 413; 568/909, 877

[56] References Cited

U.S. PATENT DOCUMENTS

| 2,644,844 | 7/1953 | Brooks et al. | 568/877 |
| 4,417,077 | 11/1983 | Drago et al. | 568/909 |
| 4,431,835 | 2/1984 | Gauthier-Lafaye et al. | 560/265 |

FOREIGN PATENT DOCUMENTS

| 46129 | 2/1982 | European Pat. Off. | 568/909 |
| 3102281A | 1/1982 | Fed. Rep. of Germany | 568/909 |

Primary Examiner—Vivian Garner
Attorney, Agent, or Firm—Brooks Haidt Haffner & Delahunty

[57] ABSTRACT

A process for the production of an ester comprises reacting an olefin with carbon monoxide, hydrogen and another ester at elevated temperature and pressure in the presence of a catalyst comprising (1) a rhodium source, (2) a ruthenium source, and (3) cobalt or zinc iodide. The product ester comprises the acid group of the ester used as reactant esterified with a hydrocarbyl group derived from the olefin, hydrogen and carbon monoxide.

12 Claims, No Drawings

PRODUCTION OF ESTERS

The present invention relates to a process for the production of a second carboxylic acid ester by reacting an olefin with carbon monoxide, hydrogen and a first ester in the presence of a catalyst.

The reaction between an olefin and carbon monoxide and hydrogen in an inert solvent to form aldehydes containing one carbon atom more than the olefin reactant is known, and such 'hydroformylation' reactions are known to be catalysed by rhodium catalysts.

Japanese patent J5 2105-590 discloses a catalytic hydroformylation process using a rhodium/phosphine catalyst which is carried out in an ester solvent. However in the process the ester acts only as a solvent and does not take part in any chemical reaction.

It has now been discovered that by carrying out the reaction between an olefin carbon monoxide and hydrogen in the presence of a first ester using a catalyst which contains (a) rhodium, (b) ruthenium and (c) cobalt or zinc iodide, a second ester is formed and that this second ester comprises the acid group of the first ester esterified with a hydrocarbyl group derived from the olefin, hydrogen and carbon monoxide. Thus if the first ester is methyl acetate and the olefin is propylene the second ester produced is butyl acetate. If the olefin however is butadiene the second ester produced can be for example but-3-enyl acetate, butane-1,4-diol diacetate or a mixture thereof.

Accordingly, the present invention comprises a process for the production of a second ester comprising an acid group derived from the first ester and a hydrocarbyl group obtained by the addition of carbon monoxide and hydrogen to an olefin characterised in that the process comprises reacting the olefin with carbon monoxide, hydrogen and the first ester at elevated temperature and pressure in the presence of an effective amount of a catalyst comprising
 (1) a rhodium source,
 (2) a ruthenium source, and
 (3) cobalt or zinc iodide.

In addition to the second ester described above, an alcohol is produced as a reaction product. Thus when ethylene is reacted with carbon monoxide, hydrogen and methyl acetate, the products of the reaction are methanol and propyl acetate.

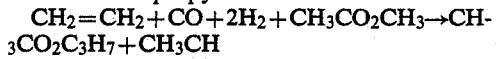
$CH_2=CH_2+CO+2H_2+CH_3CO_2CH_3 \rightarrow CH_3CO_2C_3H_7+CH_3CH$

The alcohol which is co-produced with the second ester is reactive and itself may be further carbonylated, either partially or completely to form a carboxylic acid. Thus in the reaction described above the methanol co-product can be further carbonylated to produce acetic acid.

Accordingly, in an embodiment of the present invention there is provided a process for the co-production of a carboxylic acid and a second ester comprising an acid group derived from a first ester and a hydrocarbyl group obtained by the addition of carbon monoxide and hydrogen to an olefin characterised in that the process comprises reacting the olefin with carbon monoxide, hydrogen and the first ester at elevated temperature and pressure in the presence of an effective amount of a catalyst comprising
 (1) a rhodium source,
 (2) a ruthenium source, and
 (3) a cobalt or zinc iodide.

Although any source of rhodium and ruthenium can be used, it is preferable to use a rhodium halide and a ruthenium halide. The halide may be a simple halide e.g. rhodium chloride $RhCl_3$ or ruthenium chloride $RuCl_3$ or an anionic halide complex e.g. ammonium hexachlororhodium (III) $(NH_4)_3RhCl_6$ or potassium hexabromoruthenate $K_3RuBr_6$. It is also possible to add the rhodium and ruthenium as other salts or complexes which do not contain halide whence an independent source of the halogen or halide is also added.

The rhodium source can suitably be added in amounts which constitute between 0.01 and 1% by weight of the reaction mixture, while the ruthenium halide component can suitably constitute between 0.1 and 1% by weight of the reaction mixture.

The zinc or cobalt iodide component may be added as the salt itself or may be generated in situ by adding a zinc or cobalt salt and a source of iodine or iodide, for example, a mixture of zinc acetate and iodine or cobalt carbonate and potassium iodide. Conveniently the amount of zinc or cobalt iodide added is such as to constitute between 1 and 30% by weight of the reaction mixture.

The reaction is carried out at an elevated temperature which is preferably in the range 130° to 220° C. and at elevated pressure, preferably in the range 33 and 100 bar.

Any olefin may be used as a reactant. Thus it can be a simple lower olefin, for example ethylene, propylene, a butylene isomer and the like, or it can be an olefin with more than one double bond, for example butadiene or hexatriene. The olefin may be unsubstituted or substituted with hydrocarbyl groups or other groups such as halide groups, ester groups and ether groups. The olefin may be fed to the reactor with the carbon monoxide and hydrogen if it is a gas or with the ester and catalyst if it is a liquid.

Carbon monoxide and hydrogen may be supplied to the reactors separately or as mixtures such as those derived from reactions which generate synthesis gas. The molar ratio of carbon monoxide to hydrogen, however, should be preferably in the range 1:2 to 2:1.

The reaction is preferably carried out in the liquid phase with the catalyst components in solution. The liquid reaction medium may be provided by the first ester or a mixture of the first ester and the olefin if the olefin is a liquid at the reaction temperature or a mixture of the first ester, second ester and olefin in the relative proportions such as might be found in a continuously operated reactor at steady state. It is also possible to use in conjunction with any of the liquid reaction media mentioned above, an additional unreactive organic solvent. Examples of such additional unreactive solvents are, sulpholane, chlorobenzene, methyl phenyl ether and the like.

The reaction may be carried out batchwise or continuously.

The present invention is now further illustrated by reference to the following Examples and Comparative Tests.

EXAMPLE 1

A 100 ml high pressure stirred autoclave was charged with 26 g of methyl acetate, 0.14 g of rhodium trichloride, 0.06 g of ruthenium trichloride, 0.14 g of α-picoline and 4.8 g of zinc iodide. The autoclave was sealed and flushed with carbon monoxide and pressurised to 69 bar with a 2:2:1 molar ratio mixture of carbon monoxide, hydrogen and ethylene. The autoclave was sealed and finally heated to 180° C. with stirring (1250 rpm). Rapid gas absorption occurred. After 2 hours, gas absorption had ceased and the autoclave was cooled to room temperature. The reaction mixture was analysed by gas-liquid chromatography and shown to contain 8.6% wt n-propyl acetate and 7.2% wt acetic acid.

EXAMPLE 2

Example 1 was repeated in the absence of α-picoline. The product mixture contained 9.1% wt n-propyl acetate and 6.7% wt acetic acid.

Comparative Test A

Example 1 was repeated in the absence of ruthenium trichloride. The product mixture contained only 1.3% wt n-propyl acetate.

Comparative Test B

Example 1 was repeated in the absence of rhodium trichloride. The product mixture contained no n-propyl acetate.

Comparative Test C

Example 1 was repeated in the absence of zinc iodide. The product mixture contained only 0.6% wt n-propyl acetate.

EXAMPLE 3

Example 2 was repeated at 160° C. The product mixture contained 6.7% wt n-propyl acetate and 2.1% wt 1-propanol.

EXAMPLE 4

Example 2 was repeated at 200° C. the product mixture contained 4.1% n-propyl acetate.

EXAMPLE 5

Example 2 was repeated except that 26 g of ethyl acetate was used in place of methyl acetate. The product mixture contained 7.1% wt n-propyl acetate.

EXAMPLE 6

Example 2 was repeated except that 4.5 g of cobalt iodide was used in place of zinc iodide. The product mixture contained 10.4% wt n-propyl acetate.

EXAMPLE 7

Example 2 was repeated except that 5 g of propylene was used in place of ethylene. The product mixture contained 9% wt isomeric butyl acetates.

EXAMPLE 8

Example 2 was repeated except.that 5 g of hex-1-ene was used in place of ethylene. The product mixture contained 14% wt isomeric heptyl acetates.

I claim:

1. A process for the production of a second carboxylic acid ester from a first carboxylic acid ester, an olefinic hydrocarbon, carbon monoxide and hydrogen which comprises reacting said olefinic hydrocarbon, with said carbon monoxide, said hydrogen and said first carboxylic acid ester, at elevated temperature in the range 130°–220° C. and elevated pressure in the range 33 to 100 bars, in the presence of an effective amount of a catalyst comprising
   (1) a rhodium source,
   (2) a ruthenium source, and
   (3) an iodide selected from the group consisting of cobalt iodide and zinc iodide,
   wherein the rhodium source is present in an effective amount between 0.1 and 1% by weight of the reaction mixture,
   wherein the ruthenium source is present in an effective amount between 0.1 and 1% by weight of the reaction mixture, and
   wherein the zinc iodide or cobalt iodide is present in an effective amount between 1 and 30% by weight of the reaction mixture.

2. A process as claimed in claim 1 wherein the said source of rhodium is a rhodium halide.

3. A process as claimed in claim 2 wherein the said source of ruthenium is a ruthenium halide.

4. A process as claimed in claim 1, wherein the olefinic hydrocarbon is selected from the group consisting of ethylene, propylene, a butylene isomer, hex-1-ene, butadiene and hexatriene.

5. A process as claimed in claim 1, wherein the rhodium source is rhodium trichloride, and wherein the ruthenium source is ruthenium trichloride.

6. A process as claimed in claim 1, wherein the first ester is selected from the group consisting of methyl acetate and ethyl acetate.

7. A process for the co-production of a carboxylic acid and a second carboxylic acid ester from a first carboxylic acid ester, an olefinic hydrocarbon, carbon monoxide and hydrogen which comprises reacting said olefinic hydrocarbon with said carbon monoxide, said hydrogen and said first carboxylic acid ester at elevated temperature in the range 130°–220° C. and elevated pressure in the range 33 to 100 bars, in the presence of an effective amount of a catalyst comprising,
   (1) a rhodium source,
   (2) a ruthenium source, and
   (3) an iodide selected from the group consisting of cobalt iodide and zinc iodide,
   to form a second ester and an alcohol and thereafter further carbonylating alcohol so-produced to form a carboxylic acid,
   wherein the rhodium source is present in an effective amount between 0.01 and 1% by weight of the reaction mixture,
   wherein the ruthenium source is present in an effective amount between 0.1 and 1% by weight of the reaction mixture, and
   wherein the zinc iodide or cobalt iodide is present in an effective amount between 1 and 30% by weight of the reaction mixture.

8. A process as claimed in claim 4, wherein the olefinic hydrocarbon is selected from the group consisting of ethylene, propylene, a butylene isomer, hex-1-ene, butadiene and hexatriene.

9. A process as claimed in claim 4, wherein the rhodium source is rhodium trichloride, and wherein the ruthenium source is ruthenium trichloride.

10. A process as claimed in claim 4, wherein the first ester is selected from the group consisting of methyl acetate and ethyl acetate.

11. A process as claimed in claim 7, wherein the said source of rhodium is a rhodium halide.

12. A process as claimed in claim 11, wherein the said source of ruthenium is a ruthenium halide.

* * * * *